United States Patent
Rombach

(10) Patent No.: US 7,013,700 B2
(45) Date of Patent: Mar. 21, 2006

(54) DEVICE AND METHOD FOR DETERMINING THE MOISTURE IN GASES

(75) Inventor: Martin Rombach, Lenzkirch (DE)

(73) Assignee: Testo AG, Lenzkirch (DE)

( * ) Notice: Subject to any disclaimer, the term of this patent is extended or adjusted under 35 U.S.C. 154(b) by 0 days.

(21) Appl. No.: 10/332,723

(22) PCT Filed: Jul. 4, 2001

(86) PCT No.: PCT/EP01/07654

§ 371 (c)(1),
(2), (4) Date: Apr. 29, 2003

(87) PCT Pub. No.: WO02/04933

PCT Pub. Date: Jan. 17, 2002

(65) Prior Publication Data

US 2004/0012912 A1 Jan. 22, 2004

(30) Foreign Application Priority Data

Jul. 11, 2000 (DE) .............................. 100 33 620

(51) Int. Cl.
G01N 21/00 (2006.01)
G01N 19/00 (2006.01)

(52) U.S. Cl. .................................. 73/1.06; 73/335.02

(58) Field of Classification Search ................. 73/1.03, 73/1.06, 335.02, 335.03, 335.04, 335.05
See application file for complete search history.

(56) References Cited

U.S. PATENT DOCUMENTS

| 5,345,810 A | * | 9/1994 | Rosen | 73/29.02 |
| 5,777,206 A | * | 7/1998 | Zuchner et al. | 73/29.01 |
| 5,792,938 A | * | 8/1998 | Gokhfeld | 73/29.02 |
| 5,844,138 A | * | 12/1998 | Cota | 73/335.04 |
| 6,230,543 B1 | * | 5/2001 | Froehling et al. | 73/1.06 |

FOREIGN PATENT DOCUMENTS

| DE | 3500839 A1 | * | 7/1986 | .................. 73/1.06 |
| FR | 2716975 A1 | * | 9/1995 | |

* cited by examiner

Primary Examiner—Michael Cygan
(74) Attorney, Agent, or Firm—Muirhead and Saturnelli, LLC

(57) ABSTRACT

A measuring device for measuring the moisture in gases comprises the following features: a moisture sensor and an evaluation unit connected thereto to provide a measured quantity representing a relative moisture in a gas, and a heating device which is thermally coupled to the moisture sensor. Said heating device is adapted to keep the moisture sensor at an operating temperature that is higher than the ambient temperature of the moisture sensor by an at least approximately constant difference in temperature.

15 Claims, 4 Drawing Sheets

DEVICE AND METHOD FOR DETERMINING THE MOISTURE IN GASES

BACKGROUND OF THE INVENTION

1. Technical Field

The present invention relates to a measuring device for determining the moisture in gases.

2. Description of Related Art

In measuring moisture in gases, a distinction is made between absolute humidity and relative humidity. Absolute humidity provides the mass of evaporated liquid per gas volume unit (normally in $g/m^3$). Relative humidity is the absolute humidity divided by the saturation humidity, the latter being the maximum possible mass of evaporated liquid per gas volume unit. Saturation humidity is thus a function of the temperature.

The use of capacitive moisture sensors containing a capacitor, whose capacitance varies as a function of the moisture of the gas surrounding the sensor, is known for measuring moisture in gases. Problems may occur in such sensors, in particular at high moisture levels.

There is the danger of moisture precipitating on the sensor at high moisture levels if the temperature of the moisture sensor is lower than the dew point of the surrounding gas. This results in the measured quantity being corrupted and may also result in damage to the moisture sensor if the surrounding contains chemical components which form an acid or a base on the sensor in the presence of water.

A drift in the measured quantities in the event of long-term use in an environment having a high moisture level, resulting in corruption of the measured quantities, represents another problem with conventional capacitive moisture sensors.

German Patent 28 51 686 C2 teaches that these problems may be eliminated by heating the moisture sensor to keep it above the temperature of the gas. In addition to a measured quantity delivered by the sensor, the ambient temperature and the temperature of the sensor are needed for determining the relative humidity, for which additional measurements and measuring devices are needed. In addition, a complex regulating circuit is required for this known device.

It is furthermore known from WO 97/02468 that a moisture sensor may be kept at a constant temperature, which is higher than the temperature of the gas, by heating. The known device is used for determining the absolute humidity in a gas, for which the absolute temperature of the gas, in addition to a measured quantity delivered by a moisture sensor, is needed. For this purpose, an additional measurement and an additional measuring device are required. In addition, the operating range is limited due to the constant operating temperature of the sensor. Measuring moisture without the danger of moisture formation on the sensor is only possible if the temperature of the gas is lower than the operating temperature of the sensor. In order to be able to determine the relative humidity of the gas using this known measuring device known from WO 97/02468, a correction of the measured absolute humidity value must be calculated.

SUMMARY OF THE INVENTION

The object of the present invention is to provide a moisture sensor for determining the relative moisture in gases, which is utilizable independently of the gas temperature, and for which no additional measured quantities are needed for determining the moisture content.

According to the present invention, the measuring device has, in addition to a moisture sensor and an evaluation unit connected to the moisture sensor, a heating device, thermally coupled to the moisture sensor, which is designed to keep the moisture sensor at an operating temperature which is higher than the ambient temperature by an at least approximately constant temperature difference.

In the measuring device according to the present invention, the condensation of liquid on the moisture sensor is reliably prevented by keeping the temperature of the sensor above the ambient temperature independently of the ambient temperature. In the measuring device according to the present invention, a conventional capacitive moisture sensor for determining the relative moisture in a gas may be used as the moisture sensor. These sensors have a first electrode and a second electrode and a moisture-sensitive dielectric substance between them, whose dielectric constant varies as a function of the moisture. The moisture in the surroundings is determinable via the capacitance of the capacitor by means of appropriate evaluation circuits, using such moisture sensors. Due to the elevated temperature on the moisture sensor due to heating, the measured quantity determined by the moisture sensor has a certain deviation with respect to the actual moisture in the gas, this deviation increasing with increasing temperature difference. However, this deviation of the determined value with respect to the actual value may be taken into account as early as at the time of calibration, i.e., factory adjustment, of the moisture sensor, so that during the use of the measuring device, no additional measured quantities are needed for determining the relative moisture in the gas.

According to a first embodiment of the present invention, the heating device for heating the moisture sensor has an electric heating element, which is supplied with a constant electric power. The heating element is, in particular, a heating resistor, which is connected to a constant voltage source or a constant current source. The power converted into heat in the resistor is then the square of the voltage applied divided by the resistance, or the square of the current flowing through the heating resistor multiplied by the resistance. Such a heating device, in which an electric power which is constant over time is converted into heat, makes it possible to keep the moisture sensor thermally coupled to the heating element at a temperature that is higher than the ambient temperature by an approximately constant temperature difference.

The heated moisture sensor, which is preferably a conventional capacitive moisture sensor, delivers a measured quantity which is a function of the relative moisture at the moisture sensor or in its immediate surroundings.

The relative moisture in a gas is temperature-dependent, so that heating the moisture sensor to a temperature that is higher than the gas temperature results in a deviation between the relative moisture determined by the moisture sensor and the relative moisture prevailing at a lower temperature in the remaining areas of the gas. In one embodiment of the present invention, a correction unit providing a corrected measured quantity from a first measured value determined using the capacitance of the moisture sensor is provided in the evaluation unit, this corrected quantity being proportional to the relative moisture in the gas or corresponding to the relative moisture in the gas.

The present invention furthermore relates to a method of determining the relative moisture in a gas using a measuring device which has a moisture sensor and an evaluation unit connected thereto, as well as a heating device thermally coupled to the moisture sensor. In the method according to the present invention, using the heating device, the moisture sensor is kept at an operating temperature which is higher than the ambient temperature of the moisture sensor by an at least approximately constant temperature difference.

In the method according to the present invention, an electric heating device is used in particular, which converts an electric power which is constant over time into heat and transmits it to the moisture sensor.

According to one embodiment of the method according to the present invention, the following method steps are provided for calibrating the measuring device.

In a first method step, the moisture sensor and the heating device thermally coupled thereto are introduced into a gas at a known first relative humidity and a known temperature, a first calibration value being determined using the moisture measuring device. The known first relative humidity, which corresponds to the actual moisture of the gas to be measured, represents a first corrected measured quantity for the first calibration value delivered by the moisture sensor. In a next method step, the moisture sensor and the heating device are introduced into a gas at a known second relative humidity and the known first temperature, a second calibration value being determined for the relative humidity using the moisture sensor. The known second relative humidity forms a second corrected measured quantity for the second calibration value delivered by the moisture sensor. Using the known first and second relative humidities and the first and second calibration values delivered by the moisture sensor, parameters allowing the measured quantities delivered by the moisture sensor to be recalculated into the actual values of the relative humidity are determined.

The present invention is elucidated below with reference to exemplary embodiments illustrated in the drawing.

DETAILED DESCRIPTION OF VARIOUS EMBODIMENTS

Unless otherwise stated, in the figures the same reference symbols denote the same components with the same meaning.

Figure 1:
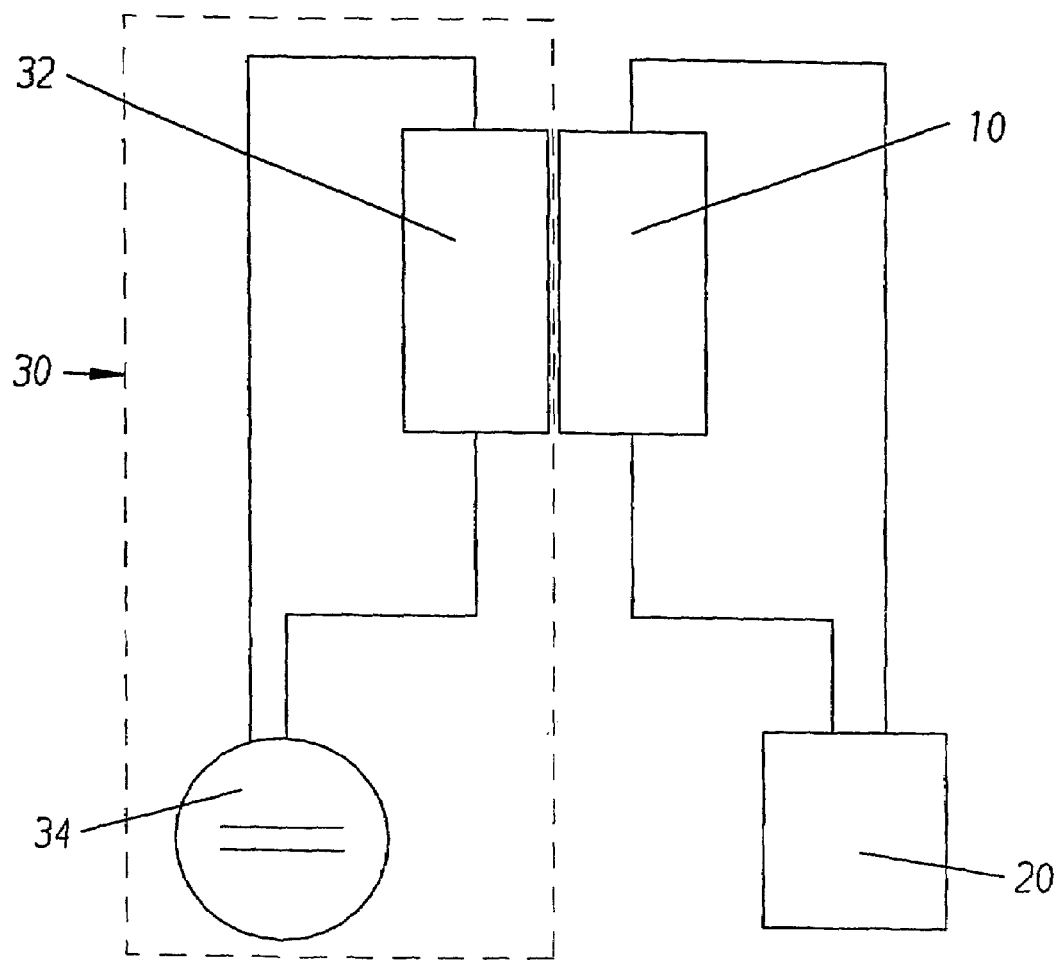
FIG. 1 shows a block diagram of a first embodiment of a measuring device according to the present invention.

FIG. 1 shows a block diagram of a measuring device according to the present invention for determining the relative moisture in gases. The measuring device has a moisture sensor 10 and an evaluation unit 20 connected to moisture sensor 10 for providing a measured quantity as a function of a relative moisture in a gas. Evaluation unit 20 has a display in particular, not shown in detail in FIG. 1, for outputting a measured quantity that has been determined, to a user. In the measuring device according to the present invention, a heating device 30 is provided for heating moisture sensor 10, a heating element 32 of the heating device being thermally coupled to moisture sensor 10. Heating device 30 is designed so that moisture sensor 10 is kept at an operating temperature which is higher than an ambient temperature of the gas to be measured by a constant temperature difference.

As a result of this heating, no moisture condenses on the moisture sensor, which could result in corruption of the measurement result and/or damage to the moisture sensor, even at a high relative humidity. In addition, heating prevents the relative humidity from reaching high values in the sensor area, which could cause drift of the measuring signal.

Figure 2:
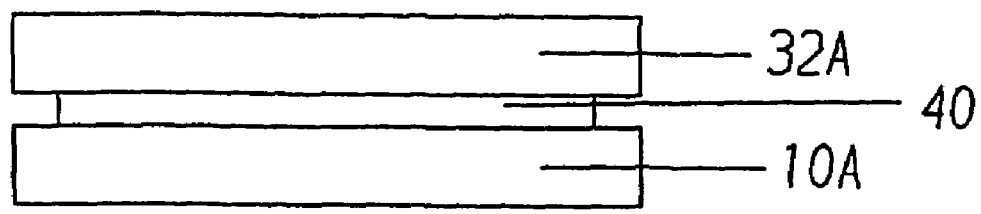
FIG. 2 shows a top view of a heating element and a moisture sensor glued to one another.
Figure 3:
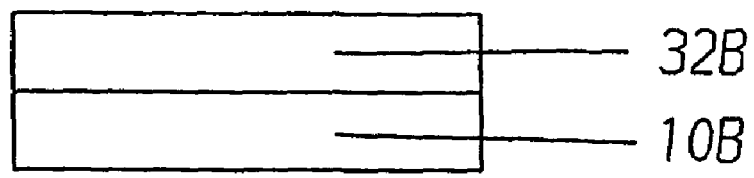
FIG. 3 shows a top view of a heating element and a moisture sensor in direct contact.
Figure 4:
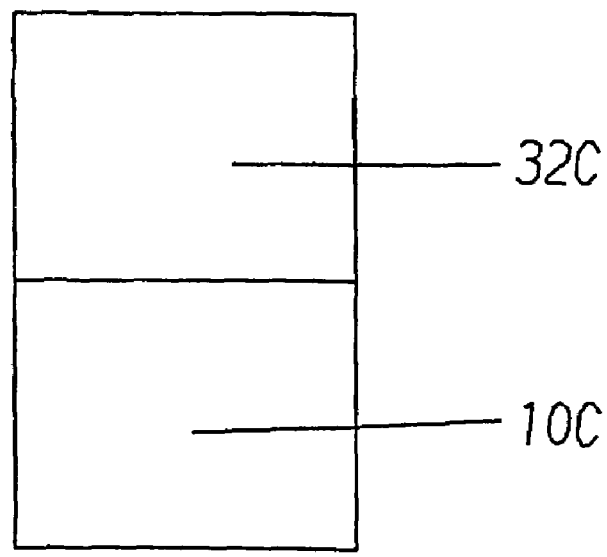
FIG. 4 shows a front view of a system of a heating element and a moisture sensor situated next to one another.

In order to keep moisture sensor 10 above the ambient temperature by the value of the temperature difference at least approximately independently of the ambient temperature, heating device 30 according to FIG. 1 is designed as an electric heating device, in which an electric power which is constant over time is converted into heat. For this purpose, heating device 30 has a constant voltage source 34, which is connected to heating element 32. Heating element 32 preferably has an ohmic resistor for converting the electric power delivered by voltage source 34 into heat or is made of such an ohmic resistor. FIGS. 2 through 4 show different exemplary embodiments for the thermal coupling of heating elements 32A, 32B, 32C and moisture sensors 10A, 10B, and 10C, respectively.

FIG. 2A shows a side view of a plate-shaped heating element 32A and a plate-shaped moisture sensor 10A, which are joined via a thermally conductive adhesive 40, which is applied between heating element 32A and moisture sensor 10A. One of the surfaces of both heating element 32A and moisture sensor 10A, which has a large surface area compared to the other surfaces of the particular element, is selected as the contact surface for adhesive 40, so that proper thermal coupling is achieved between heating element 32A and moisture sensor 10A.

In the exemplary embodiment according to FIG. 3, which also shows a side view of a heating element 32B and a thermally coupled moisture sensor 10B, heating element 32B and moisture sensor 10B are also joined on their lateral surfaces which have a large surface area compared to other lateral surfaces of the particular elements 32B, 10B, so that proper thermal coupling is achieved between heating element 32B and moisture sensor 10B. No thermally conductive adhesive is used in the exemplary embodiment according to FIG. 3. Instead, heating element 32B and moisture sensor 10B are joined directly, which may be accomplished, for example, by directly applying a heating resistor as a heating element 32B on sensor 10 using a thin-layer or thick-layer method.

FIG. 4 shows the top view of another exemplary embodiment of a system made up of heating element 32C and moisture sensor 10C, heating element 32C and moisture sensor 10C being joined on their narrower sides, so that the front and back sides of plate-shaped heating element 32C and plate-shaped moisture sensor 10C are approximately in the same plane.

Figure 5:
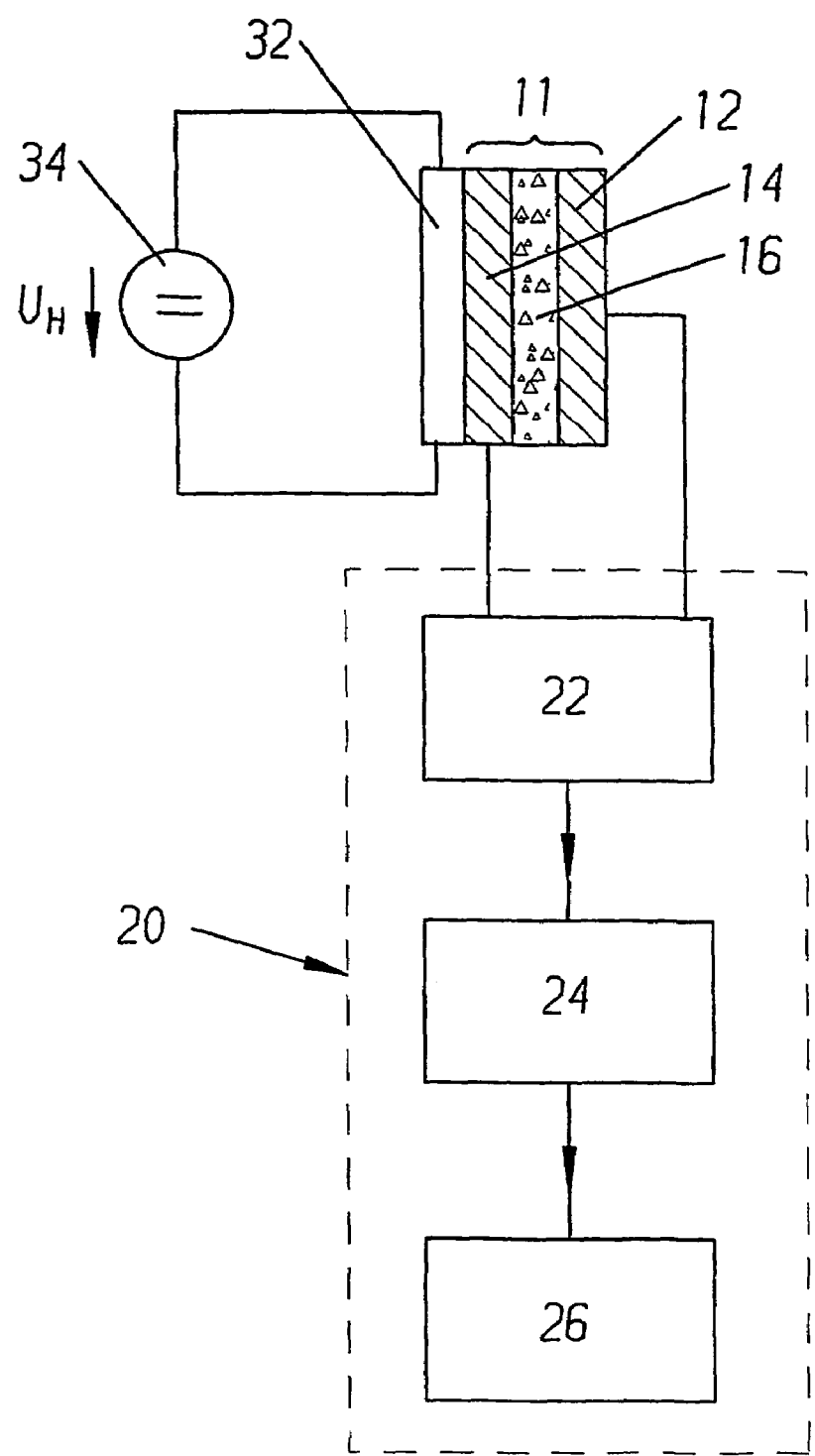
FIG. 5 shows a block diagram of an embodiment of a measuring device according to the present invention, the moisture sensor and the heating device, as well as the evaluation unit connected to the moisture sensor being shown in detail.

Moisture sensor 10 is preferably a conventional capacitive moisture sensor for determining the relative moisture in gases. The side view of such a moisture sensor 10 is schematically shown in FIG. 5. It has a first plate-shaped electrode 12 and a second plate-shaped electrode 14 and, between them, a moisture-sensitive dielectric substance 16, which form a capacitor 11. The dielectric constant of this dielectric substance 16 varies with the moisture prevailing in the area of dielectric substance 16, first electrode 12 being moisture-permeable, so that moisture may penetrate to dielectric substance 16. For this purpose, first electrode 12 is preferably made of a porous material or has a grid-type design. The value of the dielectric constant of dielectric substance 16, which varies as a function of the ambient moisture, determines the capacitance of this capacitor made up of first electrode 12, second electrode 14, and dielectric substance 16. Moisture sensor 10 is connected to evaluation unit 20 for evaluating the dielectric constant, i.e., the capacitance of the capacitor, and thus for determining the relative humidity in the surroundings of moisture sensor 10.

The evaluation unit preferably has an oscillator circuit (not illustrated), capacitor 11 being part of this oscillator circuit; the capacitance of capacitor 11 is determined using the resonance frequency of this oscillator circuit. To determine the relative humidity from the capacitance of the capacitor, i.e., the resonance frequency of the oscillator circuit, these values must be recalculated or normalized to yield the relative humidity. Due to the manufacturing tolerances during the manufacture of capacitors, the recalculation or normalization values differ from one moisture sensor to another.

An individual adjustment of the quantities determined to the actual quantities is required for each moisture sensor to eliminate these manufacturing tolerances in measuring moisture. This calibration is performed at the factory and is independent of the conditions in subsequent application, so that no subsequent adjustment of the measuring device is needed due to the application.

Calibration of a measuring device prior to first use is known and is performed using a potentiometer, for example, in the evaluation circuit, which is factory adjusted to compensate for manufacturing tolerances of the capacitor.

According to one exemplary embodiment of the present invention, the evaluation unit has a first evaluation unit 22, which delivers a first measuring signal M1, which is a function of the capacitance of the capacitor and thus of the moisture in the area of moisture sensor 10. This first measuring signal includes deviations from the actual moisture value as a result of the manufacturing tolerances of the capacitor and the heating of the moisture sensor with respect to the ambient temperature.

The relative moisture in a gas is a function of the temperature. It is obtained by dividing the absolute humidity, which provides the mass of evaporated liquid per gas volume unit by the saturation moisture, which provides the maximum possible mass of evaporated liquid per gas volume unit. At a given absolute humidity of the gas, the relative humidity decreases as the temperature increases. The value determined by moisture sensor 10 for the relative humidity is therefore always less for the measuring device according to the present invention than the actual value of the relative humidity in the gas.

Figure 6:
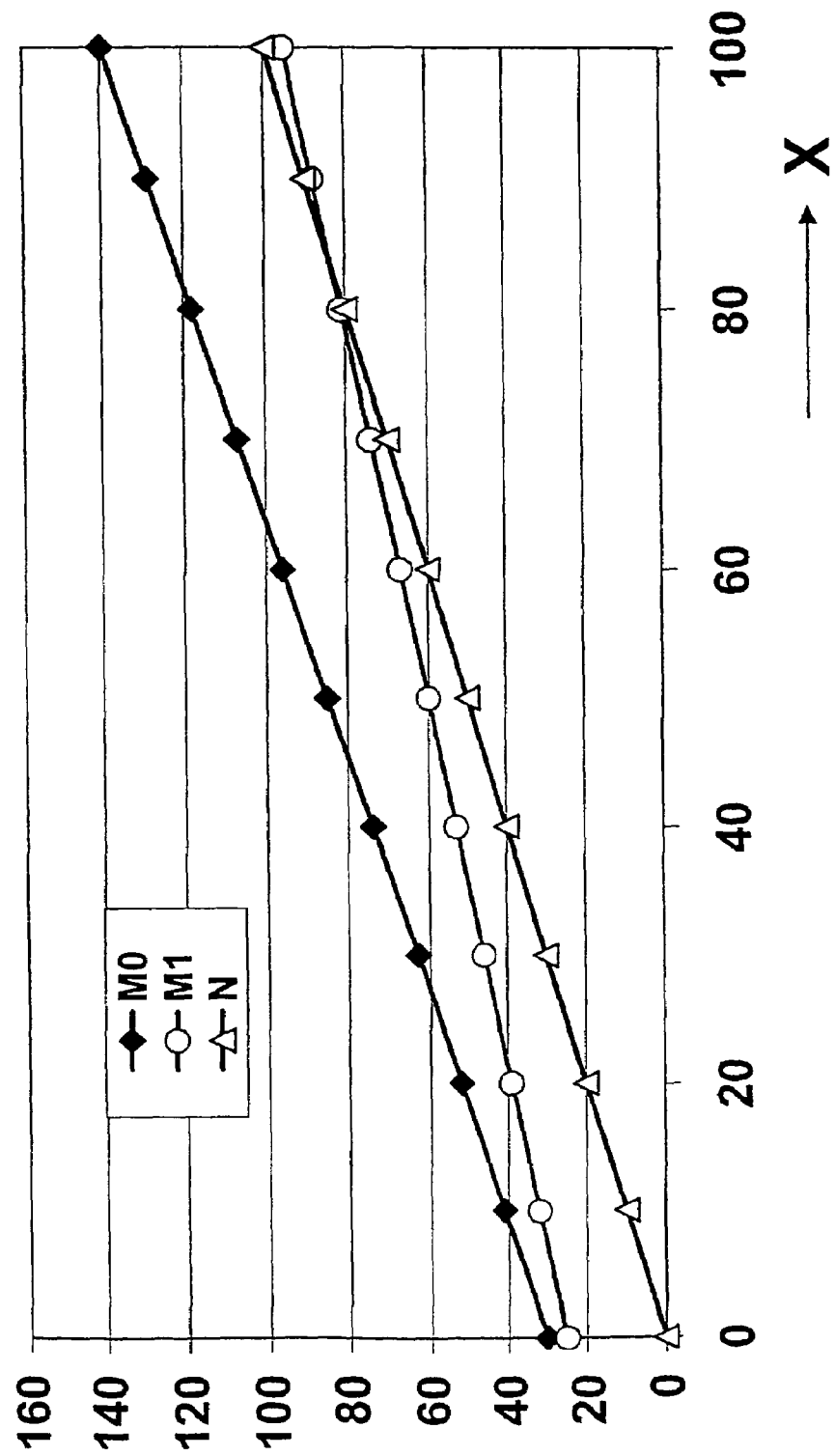
FIG. 6 shows a curve of the output signal of a moisture sensor and the actual moisture in the gas to be measured.

FIG. 6 shows first measured quantities M1 of first evaluation unit 22 for different relative humidity values between 0% and 100%. Curve N represents the actual moisture value, i.e., the desired output of the measuring device for these moisture values. As can be seen, first measured quantities M1 differ from actual measured quantities N. These differences result from manufacturing tolerances of the moisture sensor's capacitor and from the heating of the moisture sensor. For the sake of completeness, FIG. 6 shows a curve of measured quantities M0 obtained with the same moisture sensor without heating.

In the measuring device according to FIG. 5, a correction unit 24 which recalculates first measured quantities M1 into the respective corrected measured quantities N is connected downstream from first evaluation unit 22. Both the curve of first measured quantities and the curve of corrected measured quantities form a straight line, the curve of the first measured quantities satisfying the equation M1=ax+b, while the curve of the actual measured quantities satisfies the equation N=x, x representing the parameter for the actual relative moisture. It is possible to recalculate all first measured quantities M1 into actual measured quantities (normalized measured quantities) using the above relationships for M1 and N and the following formula:

$$N = 1/a \cdot M1 - b/a = c \cdot M1 - d \qquad (1)$$

In the exemplary embodiment illustrated in FIG. 6, factor c=1.43 and the additive term d=35.71.

The calculation, i.e., assignment of first measured quantities M1 to actual measured quantities N for the relative moisture may be performed in different ways.

According to one embodiment of the present invention, a computing unit which calculates the actual measured quantities N from first measured quantities M1 using equation (1) is provided in the correction unit, the actual measured quantities N being output on a display unit 26. Both parameters of equation (1) are stored in the correction unit at the time of the factory adjustment. The two parameters c, d are determined on the basis of the equation of the straight lines of first measured quantities M1. Two measured quantities for different moistures at a constant temperature are sufficient for setting up this straight-line equation.

The parameters determined for recalculating first measured quantities M1 into the output normalized measured quantities N are largely independent of the temperature. Thus, in a test of a measuring device according to the present invention, an equation for the straight line of first measured quantities M1 was obtained from only two measured quantities which were measured at a temperature of 25° C. and known relative humidity levels of 11% and 75%. Parameters c and d were determined using these two measured quantities and stored, the relative humidity of gases whose temperature was between −30° C. and 120° C. having been determined in the evaluation unit of the moisture sensor using first measured quantities M1 and equation (1), without any noticeable difference between the measurement results output and the actual values having been observed.

Another option for assigning the first measured quantities to the corrected measured quantities is storing a table containing the first measured quantities and the corresponding corrected measured quantities in the correction unit, the respective corrected measured quantity being read from the table for each first measured quantity M1 supplied to the correction unit.

For recalculating first measured quantities M1 into normalized measured quantities N, it is irrelevant whether the deviation of the curve for first measured quantities M1 from the curve for normalized measured quantities N is due to manufacturing tolerances during the manufacture of the capacitors, the heating of the moisture sensor, or to both of these effects. Conventional evaluation units of known moisture sensors, allowing the moisture sensor to be individually adjusted after manufacture, may be provided as evaluation units for the present invention.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

The invention claimed is:

1. A measuring device without a temperature sensor for measuring moisture in gases, comprising:
 a moisture sensor and an evaluation unit connected thereto for providing a measured quantity which is a function of a relative moisture in a gas; and
 a heating device thermally coupled to the moisture sensor, wherein the heating device is designed to keep the moisture sensor at an operating temperature which is higher than an ambient temperature of the moisture sensor and has an electric heating element, and wherein the evaluation unit comprises a first evaluation unit for providing a first measuring signal and a correction unit connected downstream from the first evaluation unit for determining a corrected measured quantity to the first measuring signal using stored values, wherein said stored values include at least one correction parameter of a correction function, and wherein the corrected measured quantity is determined independently of any values corresponding to a measured temperature of the moisture sensor and using said at least one correction parameter.

2. The measuring device as recited in claim 1, wherein the heating device has a heating resistor which is connected to a constant voltage source.

3. The measuring device as recited in claim 1, wherein the moisture sensor is a capacitive moisture sensor.

4. The measuring device as recited in claim 3, wherein the first measuring signal is a function of the capacitance of the moisture sensor.

5. A method of determining the relative moisture in a gas using a measuring device without a temperature sensor, which comprises a moisture sensor and an evaluation unit connected thereto, as well as a heating device thermally coupled to the moisture sensor, wherein, using the heating device the moisture sensor is kept at an operating temperature which is higher than an ambient temperature of the moisture sensor, and a corrected measured quantity is determined to the first measured quantity determined by the moisture sensor using values stored in a correction unit, wherein said values include at least one correction parameter of a correction function, and wherein the corrected measured quantity is determined independently of any values corresponding to a measured temperature of the moisture sensor and using said at least one correction parameter.

6. The method as recited in claim 5, wherein the heating device is an electric heating device which is supplied with a constant electric power.

7. The method as recited in claim 5, wherein a capacitive moisture sensor is used.

8. The method as recited in claim 6, wherein the corrected measured quantity is output to a first measured quantity.

9. The method as recited in claim 5, wherein the following method steps are provided for adjusting the measuring device:
 introducing the moisture sensor and the heating device into a gas at a known first relative humidity and a known first temperature and determining a first calibration value for the relative humidity using the moisture measuring device;
 introducing the moisture sensor and the heating device into a gas at a known second relative humidity and the first temperature and determining a second calibration value for the relative humidity using the measuring device;
 determining the at least one correction parameter for recalculating the first measured quantities into corrected measured quantities using the calibration values;
 storing the at least one correction parameter in the correction unit.

10. The method as recited in claim 5, wherein the heating device is an electric heating device which is supplied with a constant electric power, a capacitive moisture sensor is used, and the corrected measured quantity is output to a first measured quantity.

11. The method as recited in claim 9, wherein the heating device is an electric heating device which is supplied with a constant electric power, a capacitive moisture sensor is used, and the corrected measured quantity is output to a first measured quantity.

12. The measuring device as recited in claim 1, wherein the heating device has a heating resistor which is connected to a constant voltage source, the moisture sensor is a capacitive moisture sensor, and the first measuring signal is a function of the capacitance of the moisture sensor.

13. The measuring device as recited in claim 1, wherein the moisture sensor and the evaluation unit connected thereto provide a measured quantity which is a function of relative humidity of a gas at the ambient temperature.

14. The measuring device as recited in claim 1, wherein said heating device maintains the moisture sensor at an operating temperature higher than an ambient temperature by an approximately constant temperature difference.

15. The method as recited in claim 5, wherein the moisture sensor is kept at an operating temperature which is higher than an ambient temperature of the moisture sensor by an approximately constant temperature difference.

* * * * *